United States Patent [19]
Maumy et al.

[11] Patent Number: 5,507,828
[45] Date of Patent: Apr. 16, 1996

[54] ARTIFICIAL ACETABULUM

[75] Inventors: Jean Maumy, Montauban, France; Roland Willi, Neftenbach, Switzerland

[73] Assignees: Sulzer Medizinaltechnik AG, Winterthur; Protek AG, Muensingen-Bern, both of Switzerland

[21] Appl. No.: 284,770

[22] Filed: Aug. 2, 1994

[30] Foreign Application Priority Data

Aug. 30, 1993 [EP] European Pat. Off. ............ 93810616

[51] Int. Cl.[6] ........................................ A61F 2/34
[52] U.S. Cl. .............................. 623/22; 623/18
[58] Field of Search ..................... 623/16, 18, 20, 623/21, 22, 23

[56] References Cited

U.S. PATENT DOCUMENTS

| | | | |
|---|---|---|---|
| 4,936,861 | 6/1990 | Muller et al. | 623/22 |
| 4,961,748 | 10/1990 | Frey et al. | 623/22 |
| 5,074,881 | 12/1991 | Thull et al. | 623/22 |
| 5,108,448 | 4/1992 | Gautier | 623/22 |
| 5,376,122 | 12/1994 | Pappas et al. | 623/22 |

FOREIGN PATENT DOCUMENTS

| | | |
|---|---|---|
| 0253941 | 1/1988 | European Pat. Off. . |
| 0281984 | 9/1988 | European Pat. Off. . |
| 0445068 | 9/1991 | European Pat. Off. . |
| 0490616 | 6/1992 | European Pat. Off. . |
| 0551794 | 7/1993 | European Pat. Off. . |

*Primary Examiner*—David Isabella
*Attorney, Agent, or Firm*—Townsend and Townsend and Crew

[57] ABSTRACT

The acetabulum has an outer shell (1) which is composed of several relatively rigid outer shell segments (1a, 1c) that are interconnected by resilient regions. The outer shell (1) has regions of high shape stability which are elastically connected to each other. The outer shell segment (1) in the region of the direction of main loading (F) is made as an attachment zone (1a) and has apertures for bone screws and a guiding and attachment bore (3) for an inner shell (10). The guiding bore (3) is with respect to the whole outer shell (1) situated at the pole (P2). In the region of main loading (F) the outer shell (1), that is the attachment zone (1a), bears, engaged by shape, onto the inner shell (10), whereas the remaining outer shell segments (1c) have a spacing (D) from the inner shell (10), so that by the bell-like suspension of the inner shell (10) at the pole (P2) the inner shell is movable, particularly perpendicularly, to the axis (18), while damping elements (13a) of the inner shell (10) transmit onto the outer shell (1) particularly impact forces in a dampened manner.

10 Claims, 4 Drawing Sheets

(A-A)

(C)

ARTIFICIAL ACETABULUM

BACKGROUND OF THE INVENTION

The invention relates to an artificial acetabulum made of an outer shell which houses an inner shell that cooperates with a spherical head of the joint.

Artificial acetabula are often made as double shells in which the outer shell permits attachment in osseous tissue, and the inner shell has a spherical surface to receive the spherical head of a prosthesis shaft. The outer and inner shells may be of different materials, to use, on the one hand, an outer shell which is tissue-tolerated as regards growing-in, and, on the other hand, to use for the inner shell materials, which have good properties as regards wear and anti-seizure behavior.

European patent publication EP 0 313 762 A1 is known an acetabulum in which the inner shell of plastics is fixed in the outer shell with a snap connection. The outer shell has a high rigidity which causes a high shape stability. The inner shell of plastics is elastically deformable, depending on the influence of forces acting through the spherical head, and is supported in this by the rigid outer shell. However, the rigid outer shell has the disadvantage that, in the case when the bone elastically yields under high compressional forces, tensile and shearing forces act on the side relieved of load between the outer shell and the bone.

European patent publication EP 0 445 068 A1 discloses a two-part acetabulum in which the outline of the outer shell may follow small changes of the supporting osseous tissue and thereby offers equalization of forces to the osseous tissue. Both shells are made of metal, the wall thickness of the outer shell being very thin compared to the wall thickness of the inner shell. The inner shell has the disadvantage that it must be made of metal to ensure a high shape stability of the inner surface on which the spherical head bears. The elastic outer shell has the disadvantage that, immediately after implantation, the in growth of bone is in some cases more difficult because during the growing-on relative movement might be possible. Furthermore, the elastic outer shell may follow the subsequently acting tensile and compressional forces between the outer shell and the bone only within the scope of its elastic pre-deformation during primary attachment.

SUMMARY OF THE INVENTION

It is an object of the invention to devise a two-part acetabulum which avoids the mentioned disadvantages. This is achieved by providing the outer shell with an attachment zone and, in the peripheral direction, with resilient regions of smaller wall thickness that alternate with outer shell segments of greater wall thickness. The attachment zone comprises attachment means and guiding means, and the outer shell has on the side opposite the attachment zone a recess which is open towards the base or equator of the outer shell and extends along a meridian line which passes through the pole of the shell. Further, the inner shell has on its outer surface a ring-shaped dampening element.

The acetabulum of the present invention has various advantages. The outer shell is composed of several, relatively rigid outer shell segments which are interconnected by resilient regions. The outer shell has therefore regions of high shape stability which are elastically interconnected. The outer shell segment in the region of the direction of main load is made as an attachment region and has apertures for bone screws and also a guiding and attachment bore for the inner shell. The guiding bore is with respect to the whole outer shell situated at the pole. The inner shell of the acetabulum according to the invention may be made of metal or plastics. In the region of the direction of main load the outer shell, i.e. the attachment zone, is supported by the inner shell, which, when the latter is made of plastics, impedes plastic deformation. The remaining outer shell segments do not bear directly on the inner shell. Due to the bell-like suspension of the inner shell in the guide bore of the outer shell, the inner shell is movable, particularly in a radial direction. The dampening elements dampen or cushion the transmission of forces, especially impact forces from the inner shell to the outer shell.

The elastically interconnected outer shell segments can follow the movement of the bone so that, for instance, the osseous tissue grown onto the outer shell is not torn off. Particularly advantageous is the use of resorbable auxiliary bodies which, inserted between the recesses of the outer shell segments, give the outer shell during a fairly long period a high shape stability. Small relative movement takes place between the outer shell and the bone and the osseous tissue may grow successfully onto the outer surface of the outer shell. After the implantation, the rigidity of the outer shell is for a fairly long time reduced by the degradation of the resorbable auxiliary bodies, so that the outline of the outer shell may follow the changes of the grown-on, supporting osseous tissue and care is taken for force equalization to the osseous tissue.

The inner shell is made, in a manner known per se, of a plastics used in the implantation technology, for instance polyethylene, or of a body-tolerated metal. The outer shell is of a body-tolerated metal, for instance pure titanium or a titanium alloy.

The invention will now be described, by way of example, with reference to embodiments.

BRIEF DESCRIPTION OF THE DRAWINGS

FIG. 1b is a section through the outer shell along line A—A in FIG. 1a;

DESCRIPTION OF THE PREFERRED EMBODIMENTS

Figure 1A:
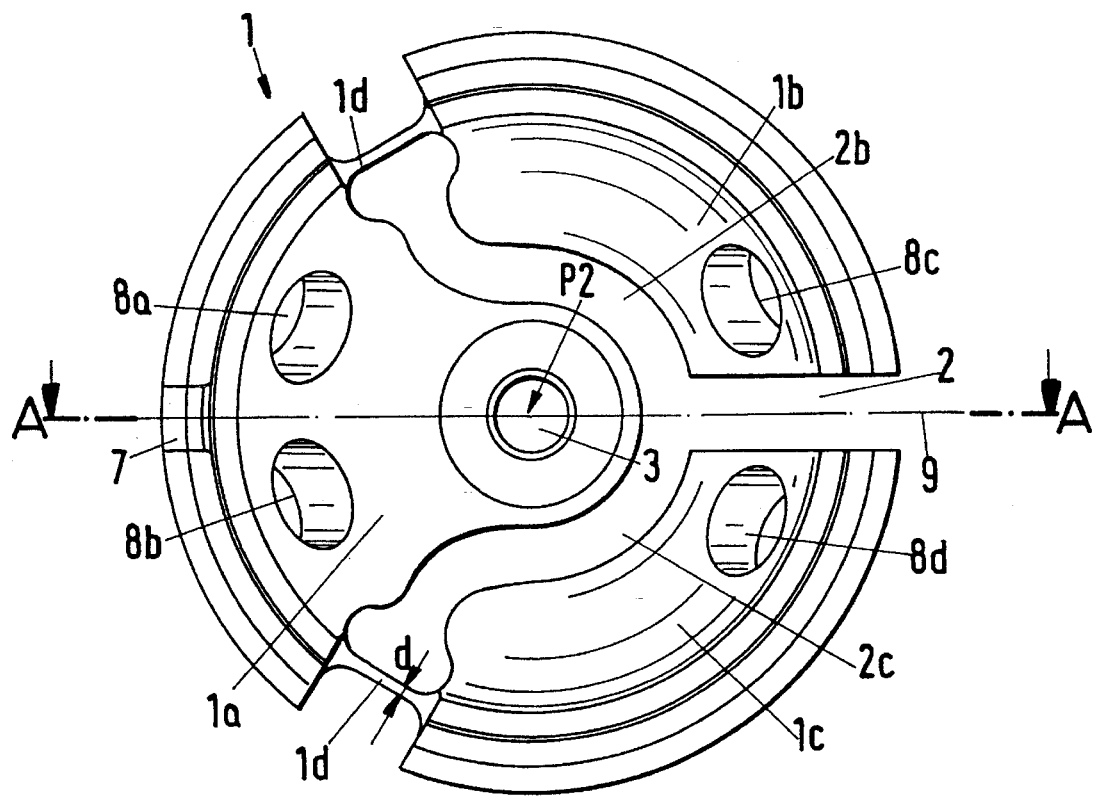
FIG. 1a is a view from below of an outer shell.
Figure 1B:
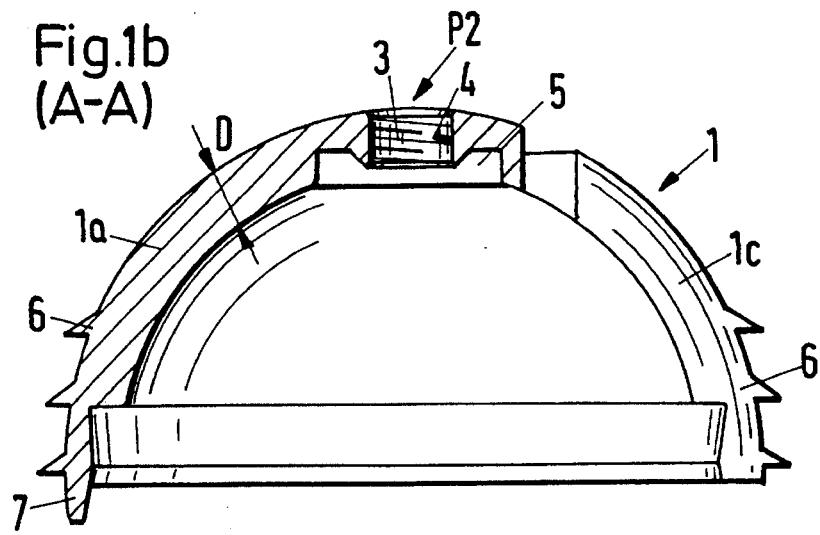

FIG. 1 shows a view from below into the opening of a metallic outer shell 1, which is formed substantially by an attachment zone 1a and two outer shell segments 1b and 1c, which are connected by resilient connection elements 1d to the attachment zone 1a. The attachment zone 1a may be primarily attached in osseous tissue by attachment means, such as spines 6 or bone screws which extend through bores 8a, 8b. The position of the pole P2 can be seen in FIGS. 1a and 1b. The pole P2, which forms part of the attachment zone 1a, is situated, with respect to the whole outer shell 1, at its pole. In the region of the pole P2 is a centering or guiding bore 3 which extends along an assembly axis 18 (shown in FIG. 3); the bore 3 has a smooth inner surface or is provided with a thread 4. The centering bore 3 extends into a conical, outwardly open recess 5. In the region of the equator of the outer shell 1 is at each side of the attachment zone 1a provided a spring element 1d, which extends in the peripheral direction, has a width d and each connects one outer shell segment 1b, 1c to the attachment zone 1a. The outer shell segments 1b, 1c can also be primarily attached in osseous tissue by attachment means, such as spines 6 or bone screws which extend through the bores 8c, 8d. In the present example an S-shaped recess 2b, 2c is formed between the outer shell segments 1b, 1c and the attachment zone 1a. Between the outer shell segments 1b, 1c is formed a radial recess 2 extending in the direction of a meridian circle 9. The extension of the recesses 2, 2b, 2c and also their width may be carried out in a number of embodiments. The resilient properties between an outer shell segment 1b, 1c and the attachment zone 1a may be varied within wide limits by the arrangement and design of the spring element 1d. The illustrated spring element 1d has in the radial direction a relatively small wall thickness d, and in its extension parallel to the assembly axis 18 a wall thickness d2, which is greater than the wall thickness d. As is best seen in FIG. 1a spring element 1d is least rigid during compression or expansion of the outer shell 1 in the peripheral direction. The resilient properties between the attachment zone 1a and the outer shell segments 1b, 1c may be varied, within wide limits, in dependence on the arrangement and the design of spring element 1d.

Figure 1C:
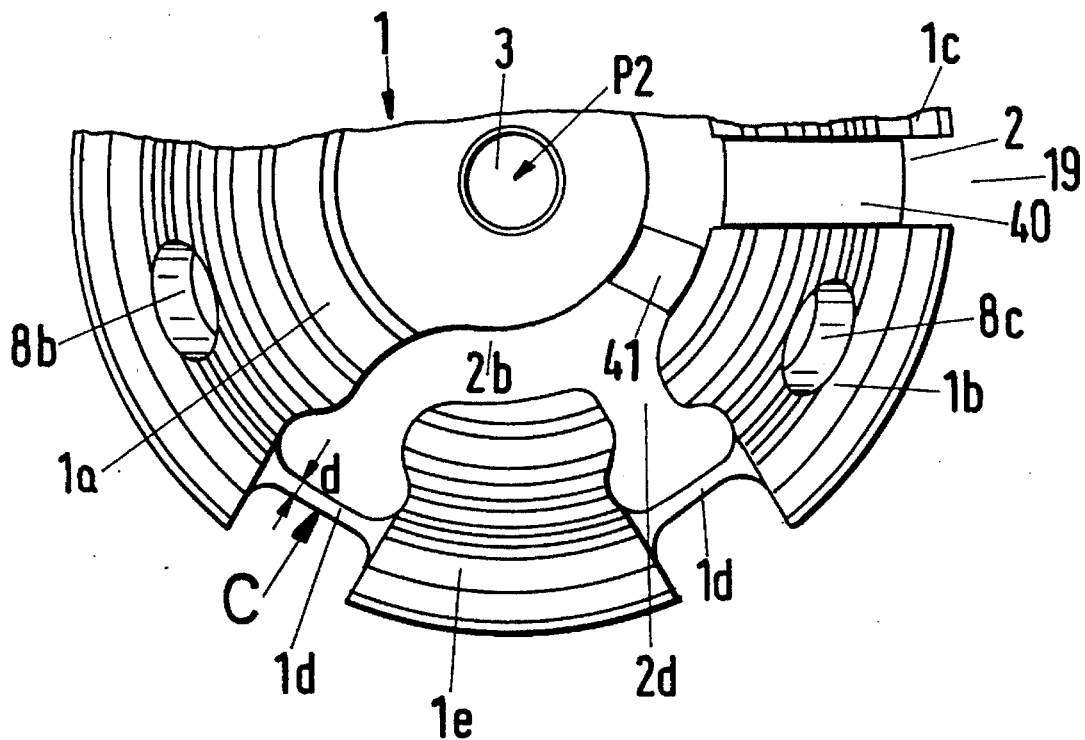
FIG. 1c is a plan view of a further outer shell.

FIG. 1c shows a plan view of a further embodiment of an outer shell 1. The attachment zone 1a is of the same design as that in FIG. 1a and has therefore a bore 8b, a pole P2 with a centering bore 3 and a spring element 1d extending in peripheral direction. After the spring element 1d follow, in the peripheral direction, several outer shell segments 1e, 1b, which are interconnected in each case by at least one spring element 1d. Between the outer shell segments are recesses 2b, 2d, which are bridged only by spring elements 1d. The outer shell segments 1e, 1b may have bores 8c for the attachment of the outer shell segment to the bone with a bone screw.

Figure 1D:
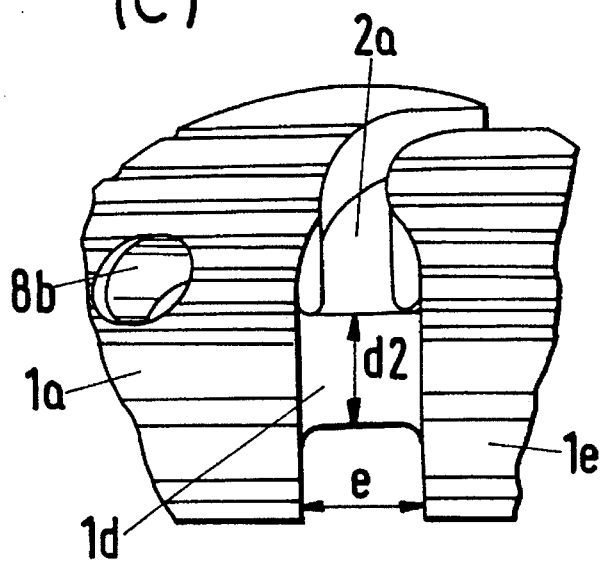
FIG. 1d is a side elevation of the outer shell taken in the direction of arrow "C" in FIG. 1c.

FIG. 1d shows a side elevation of spring element 1d, which has a height d2 and bridges a recess width e between the attachment zone 1a and the outer shell segment 1e. The extension of the recess between the attachment zone 1a and the outer shell segment 1e may be designed in a number of ways, for instance as shown, such that the recess width narrows after the spring element 1d. A recess 2a may, naturally, also widen along its way, and may also have parallel side walls or side walls making an angle with each other. For every outer shell segment 1e, 1b is needed at least one spring element 1d to obtain a continuous connection to the attachment zone 1a. In the illustrated embodiment the spring elements are arranged along the peripheral direction of the outer shell 1. Depending on the desired spring action, the spring elements 1d can also be situated at other places to obtain direct connection between the outer shell segment 1e, 1b and the attachment zone 1a, or to connect together outer shell segments 1e, 1b. Outer shells 1 are normally symmetrical, so that the plane 19 shown in FIG. 1c is a plane of symmetry, and a recess 2 is therefore between the outer shell segments 1b, 1c.

To insert the outer shell 1 into a recess in the bone the outer shell segments 1c, 1b, 1e may be grasped by a tool and pre-tensioned against the assembly axis 18 in such a way, that the diameter of the shell periphery is reduced so that the outer shell can be seated in the prepared recess in the bone. After insertion, the outer shell expands and assumes the necessary spherical inner surface. The rigidity of the outer shell 1 may be increased, for instance during insertion, by inserting removable bodies 40, 41 between the outer shell segments 1b, 1e and the attachment zone 1a. As a consequence, when it is driven home into the recess in the bone, the outer shell 1 is very rigid.

During the driving home of the outer shell 1 the edges of the recess in the bone are additionally injured by the attachment means 6 which may, however, be beneficial for the growth of the bone onto the outer surface of the outer shell 1. It may be advantageous if the outer shell 1 is, during the first months after implantation, very rigid to enable the bone to grow onto the outer surface of the outer shell 1 without any problems. This may be achieved if, before or during the driving of the outer shell 1 home into the recess in the bone, bodies 40, 41 of resorbable material are inserted into the recesses 2, 2b, 2d. The resorbable bodies 40, 41 give to the outer shell 1 initially rigid properties, while the bodies 40, 41 after a fairly long time degrade and lose their supporting function.

Figure 2A:
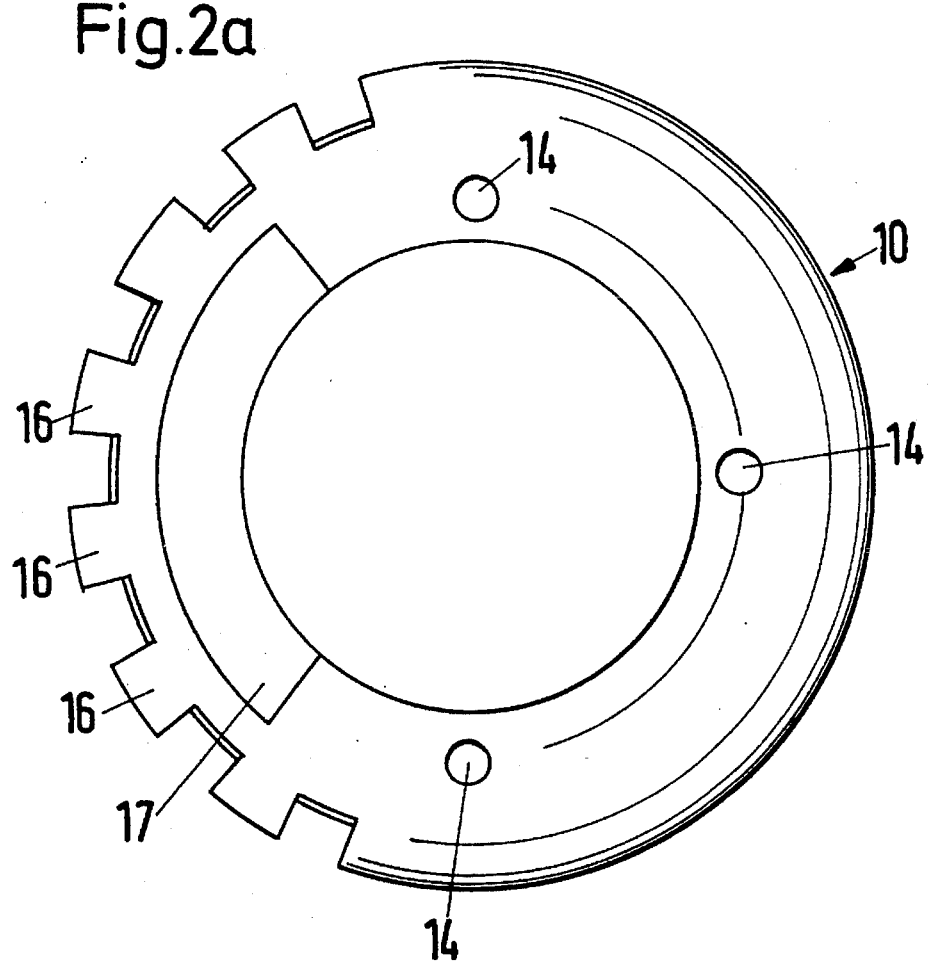
FIG. 2a is a view from below of an inner shell.
Figure 2B:
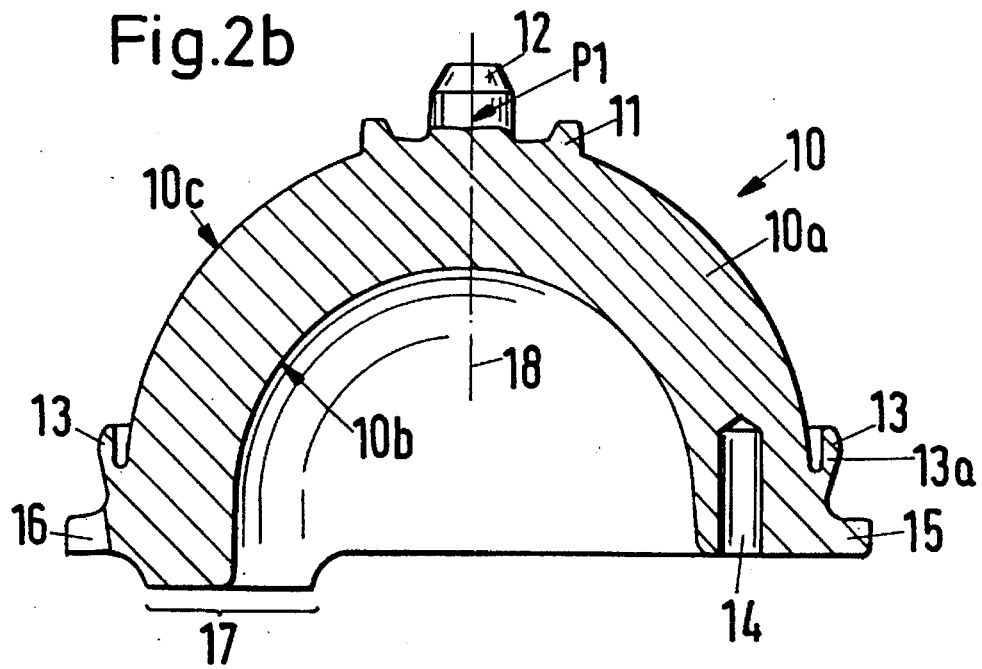
FIG. 2b is a side-elevational section through the inner shell.

FIG. 2b shows a section through an inner shell 10 a pole P1 of which is situated at a centering pin 12. A ring-shaped, locally deformable projection 11 is coaxial with the centering pin 12. The inner shell 10 has on its equator a projecting collar 15 which is partly perforated whereby several projections 16 are formed which extend radially outwardly. The outer surface 10c has adjacent the collar 15 an elastic support element 13 which extends annularly about the inner shell 10 and in the present embodiment was made from the wall 10a of the inner shell 10, in that the projecting region 13 of the inner shell 10 was cut so that a resilient lip 13a was made which forms part of the inner shell 10. The inner surface 10b of the inner shell 10 is spherical to support the spherical head of a joint shaft.

FIG. 2a is a view from below of the inner shell 10. The three bores 14 serve for the grasping of the inner shell 10 with a holder (not shown) and its insertion into the outer shell 1. Also visible are radially outwardly extending projections 16 and a step 17 which is situated on the side of entry of the highest forces.

Figure 3:
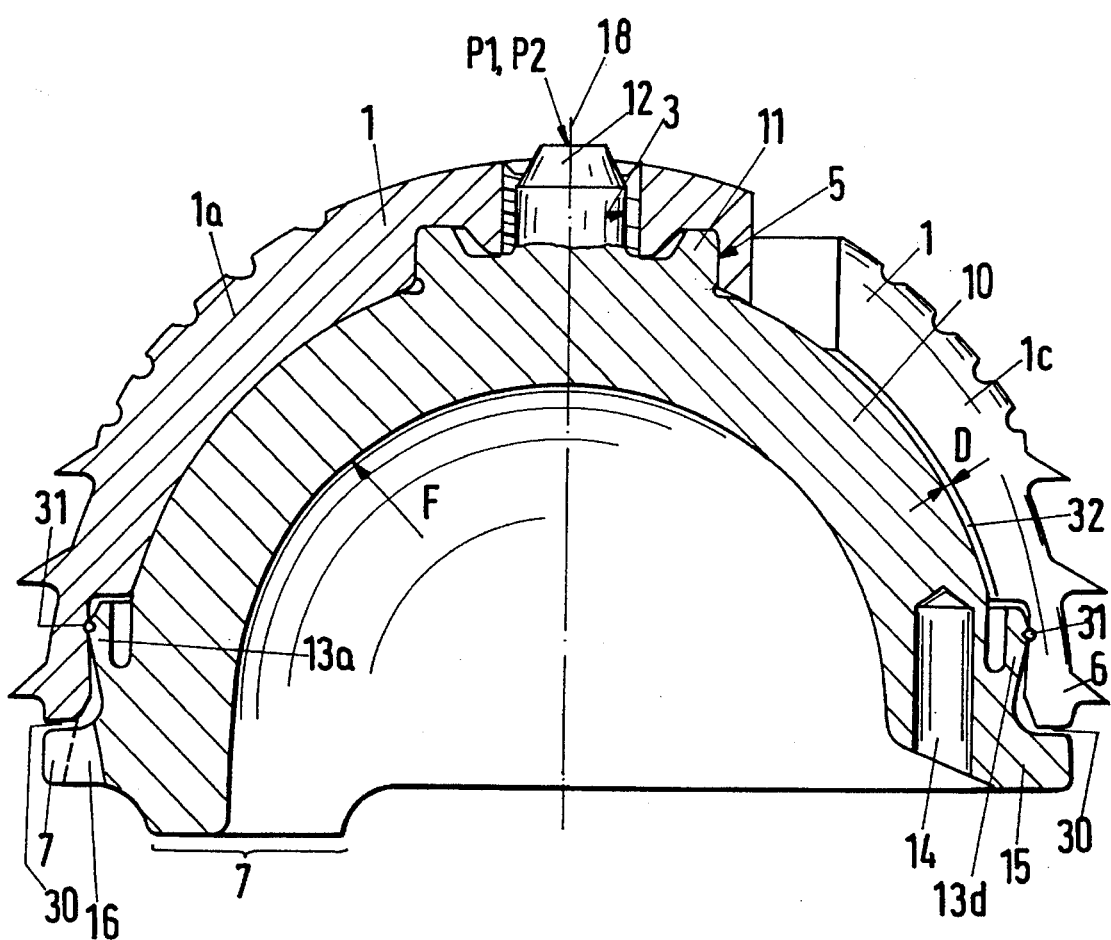
FIG. 3 is a side-elevational section through a two-part acetabulum.

FIG. 3 shows the two-part acetabulum of the present invention in its assembled state. After the outer shell 1 has been fixed in the bone, the inner shell 10 is grasped with a holder, which engages bores 14, and is inserted in the direction of the assembly axis 18 into the outer shell 1. The centering pin 12 of the inner shell 10 and the guiding bore 3 of the outer shell 1 serve for the centering and guiding of the inner shell 10 as it is pressed into the outer shell. The centering pin 12 forms with the guiding bore 3 a connection by shape or by friction. During assembly the annular projection 11 of the inner shell 10 enters the conical recess 5 of the outer shell 1 and forms also a connection by shape or friction, usually a snap fastener. During assembly the ring-shaped projection 11 of the inner shell 10 enters the conical recess 5 of the outer shell 1 and also forms a connection by shape or friction, usually a snap fastener. In the region of the equator the resilient lip 13a of the elastic support 13 bears against the inner surface of the outer shell 1, while the inner diameter of the outer shell 1 in this region slightly increases towards the pole P1, so that a snap fastener is formed in the region of the equator between the inner shell 10 and the outer shell 1. The attachment zone 1a of the outer shell 1 has a projection 7 extending in the direction of the assembly axis 18.

The mutual position of the inner shell 10 and the outer shell 1 in their equatorial alignment may be determined directly before the insertion of the inner shell 10. The inner shell 10 has radially outwardly extending projections 16. The inner shell 10 must be inserted into the outer shell 1 in such a way that the projection 7 lies between two projections 16, so that the inner and outer shells are fixed in the pressed-in state as regards their mutual movement in the equatorial direction.

The inner and outer shell are firmly connected together at their common poles P1, P2, whereas the inner shell 10 bears elastically with its resilient lip 13a in the region of the equator on its whole periphery against the outer shell 1, thereby forming a seat 31 such that the inner shell 10 can perform a rocking motion in a direction perpendicular to the assembly axis 18.

When subjected to forces, the two-part acetabulum exhibits both static and dynamic behavior. In the static case, which is illustrated in FIG. 3, the inner surface of the attachment zone 1a bears against the outer surface of the inner shell 10. The approximate direction of a reaction force F, exerted by a spherical head on an acetabulum is towards the attachment zone 1a as can be seen in FIG. 3. The attachment zone 1a consequently supports the inner shell 10 in the region of the highest static loading. It is therefore possible to make the inner shell 10 of plastics, because the supportive action prevents the plastics from flowing. In the static case the movable regions 1b, 1c have a spacing D from the outer surface of the inner shell 10. When subjected to dynamic loading the impacting reaction forces are transferred by the spherical head onto the inner shell 10 in all possible directions. The inner shell 10 is only lightly supported in the direction of movable regions 1b, 1c, so that the inner shell 10 tries to turn to this direction and a rocking movement of the inner shell 10 about the pole P1, P2 results. The pressure peaks are transferred to the movable regions 1b, 1c of the outer shell 1, which transfer them, dampened, to the osseous tissue. The movable regions 1b, 1c of the outer shell 1 follow the movements of the osseous tissue, so that the grown-in osseous tissue is not released from the outer surface of the movable regions 1b, 1c even at high pressure peaks. The collar 15 and also the projection 16 of the inner shell 10 are spaced from the outer shell 1 by a spacing 30, which is eliminated only at high pressure peaks and limits the relative movement between the inner and outer shells.

The outer shell 1 adapts itself elastically both in the case of acting forces and in the case of small changes of the osseous tissue, so that the tensile and shearing forces between the outer shell 1 and osseous tissue remain relatively small.

What is claimed is:

1. An artificial acetabula cup prosthesis comprising:

a metallic outer shell for attachment to the acetabulum; and an inner liner for receipt of a spherical head, the liner having an outer surface shaped to be inserted within the outer shell, a centering pin, and a circumferential dampening element on the outer surface for attaching the liner to the outer shell;

the outer shell having a base region and an opposite polar region which includes a guiding means that is coaxial with a rotational axis of symmetry of the outer shell and is shaped to receive the centering pin, the outer shell defining a wall having resilient regions of circumferentially spaced relatively thin wall segments alternating with relatively thick wall segments, the thick wall segments including means for attaching the outer shell to natural bone, the guiding means and an area including at least a part of at least one of the thick wall segments defining an attachment zone between the outer shell and the natural bone;

the outer shell further comprising on a side generally opposite to the attachment zone an elongated opening formed in the wall which extends along a meridian arc from the base to the polar region.

2. A device according to claim 1 wherein the inner shell is made of metal.

3. A device according to claim 1 wherein the inner shell is made of plastics.

4. A device according to claim 1 wherein the dampening element is made of polyethylene.

5. A device according to claim 3 wherein the dampening element is part of the inner shell and wherein the outer surface of the inner shell proximate the base is undercut and defines a resilient lip.

6. A device according to claim 1 wherein the attachment zone of the outer shell contacts the inner shell over a relatively large surface, and including a spacing between a portion of the outer shell segments and a portion of the inner shell.

7. A device according to claim 1 wherein the dampening element bears radially against a recess in the outer shell and forms a snap fastener.

8. A device according to claim 1 wherein at least two outer shell segments comprise attachment means.

9. A device according to claim 1 including a resorbable body inserted into at least a portion of the opening to thereby increase the rigidity of the outer shell.

10. A device according to claim 9 wherein the resorbable bodies are made of polylactate.

\* \* \* \* \*